United States Patent [19]

Kordes

[11] Plant 4,044

[45] Apr. 26, 1977

[54] ROSE PLANT

[75] Inventor: Reimer Kordes, Sparrieshoop, Germany

[73] Assignee: Jackson & Perkins Co., Medford, Oreg.

[21] Appl. No.: 671,171

[22] Filed: Mar. 29, 1976

[51] Int. Cl.[2] ..... A01H 5/00

[52] U.S. Cl. ..... Plt./24

[58] Field of Search ..... Plt./24

*Primary Examiner*—Robert E. Bagwill

*Attorney, Agent, or Firm*—Klarquist, Sparkman, Campbell, Leigh, Hall & Whinston

EXEMPLARY CLAIM

1. A new and distinct cultivar of rose plant of the floribunda class, substantially as herein shown and described, characterized particularly as to novelty by the unique combination of a bushy, heavily branched plant, high greenhouse production of buds of a clear Buttercup Yellow (W), whose shape is oval but with a blunt or flat tip; Spinach Green (W) glossy foliage and a strong fragrance.

1 Drawing Figure

1

This invention relates to a new and distinct cultivar of rose plant of the floribunda class, originated by me by crossing the cultivar Mabella, with pollen from the cultivar Minigold.

The primary objective of this breeding was to produce a new and improved cultivar of the floribunda class bearing pure, clear yellow buds and blooms on plants especially suitable for production of cut flowers in greenhouses.

This objective was fully achieved along with other desirable traits as evidenced by the following unique combination of characteristics which are outstanding in the new cultivar and which distinguish it from its parents as well as from all other cultivars of which I am aware:

1. A bushy, compact plant, making numerous new branches, or canes, from the base of the plant.
2. A habit of growth similar to the cultivar Mercedes, U.S. Plant Pat. No. 3,724.
3. A long, oval bud form with a blunt or flat tip.
4. Very, stiff petals which are near Buttercup Yellow.
5. A high centered open flower of approximately 35–40 flowers.
6. A strong, pleasant fragrance.
7. Glossy, Spinach Green foliage.

Asexual reproduction of this new cultivar by budding as performed at Elmshorn, Holstein, W. Germany and near Irvine, Calif., shows that the aforementioned characteristics come true to form, and are established and are transmitted through succeeding propagations.

The accompanying illustration shows typical specimens of the vegetative growth and flowers of this new cultivar in different stages of development and as depicted in color as nearly true as it is reasonably possible to make the same in a color illustration of this character.

The following is a detailed description of my new rose cultivar, with color terminology in accordance with *Wilson's Horticultural Color Chart*, except where ordinary meanings are applicable:

Parentage:
- *Seed Parent.*—Mabella.
- *Pollen Parent.*—Minigold.

Classification:
- *Botanical.*—Rosa hybrid.
- *Commercial.*—Floribunda.

2

FLOWER

Observations were made at Irvine, Calif., in February, 1976 from plants grown in greenhouse.

Blooming habit: Recurrent; continuous.

Bud:
- *Size.*—1 to 1¼ inches when petals start to unfurl.
- *Form.*—Long, oval, blunt top.
- *Color.*—When sepals first divide: Near Buttercup Yellow (5/1). When half blown; upper side of petals: Near Buttercup Yellow (5/1). Lower side of petals: Near Buttercup Yellow (5/1).
- *Sepals.*—Color: Outer surface — near Scheeles Green (860/3), slightly hairy. Three appendaged sepals, normally appendaged. Two unappendaged sepals, hairy edged.
- *Receptacle.*—Color: Near Scheeles Green (860/3). Shape: Funnel. Size: Large, broad. Surface: Slightly hairy.
- *Penduncle.*—Length: Short. Surface: Glandular with long stipitate glands. Color: Light green. Strength: Stiff, erect.
- *Opening.*—Slowly; outer petals slightly pointed; inner petals more undulated and recurved.

Bloom:
- *Size.*—Medium. Average open size: 3½ inches.
- *Borne.*—Singly and in clusters. If in clusters: Flat.
- *Stems.*—Medium.
- *Form.*—When first open: High centered. Permanence: Outer petal edges slightly curled.
- *Petalage.*—Number of petals under normal conditions: 35–40.
- *Color.*—Center of flower: Upper side of petals — Buttercup Yellow (5/1); reverse side of petals — Buttercup Yellow (5/1); base of petals — near Buttercup Yellow (5); general tonality from a distance — Buttercup Yellow (5/1).
- *Discoloration.*—General tonality at end of first day: Buttercup Yellow (5/1); third day — near Buttercup Yellow (5/2).
- *Fragrance.*—Strong.

Petals:
- *Texture.*—Thick, very rigid.
- *Shape.*—Round.
- *Form.*—Tips slightly recurved.
- *Arrangement.*—Imbricated. Petaloids in center: Few.

*Persistence.*—Drop off cleanly.
*Lastingness.*—On the plant: As cut flower — Very long.

Reproductive Parts:
*Anthers.*—Medium. Color: Yellow. Arrangement: Regular around styles.
*Filaments.*—Color: Yellow.
*Pollen.*—Gold yellow.
*Styles.*—Color: Pale Pink.
*Stigmas.*—Color: Yellow.

PLANT

Form: Bush.
Growth: Vigorous, branching.
Foliage: Number of leaflets on normal mid-stem leaves: 5 or 7.
*Size.*—Large.
*Quantity.*—Normal.
*Color.*—New foliage: Near Spinach Green (0960/3) overlaid slightly with Garnet Brown (00918/3). Old foliage: Near Spinach Green (0960).
*Shape.*—Oval pointed.
*Texture.*—Upper side: Glossy.
*Edge.*—Serrated, slightly undulated.
*Serration.*—Single, small.
*Petiole.*—Rachis: Color — green. Upper side: Small prickles along edges. Underside: Large prickles.

*Stipules.*—Long, bearded.
*Disease Resistance.*—Resistant to mildew under normal growing conditions at Irvine, Calif.

Wood:
*New Wood.*—Color: Light green. Bark: Smooth.
*Old Wood.*—Color: Green. Bark: Smooth.

Prickles:
*Quantity.*—On main stalks from base: Ordinary. On laterals from stalk: Ordinary.
*Form.*—Oval base and long, straight, hooked downwardly.
*Color when young.*—Brown.
*Position.*—Irregular.

Small Prickles:
*Quantity.*—On main stalks: None. On laterals: None.

I claim:

1. A new and distinct cultivar of rose plant of the floribunda class, substantially as herein shown and described, characterized particularly as to novelty by the unique combination of a bushy, heavily branched plant, high greenhouse production of buds of a clear Buttercup Yellow (W), whose shape is oval but with a blunt or flat tip; Spinach Green (W) glossy foliage and a strong fragrance.

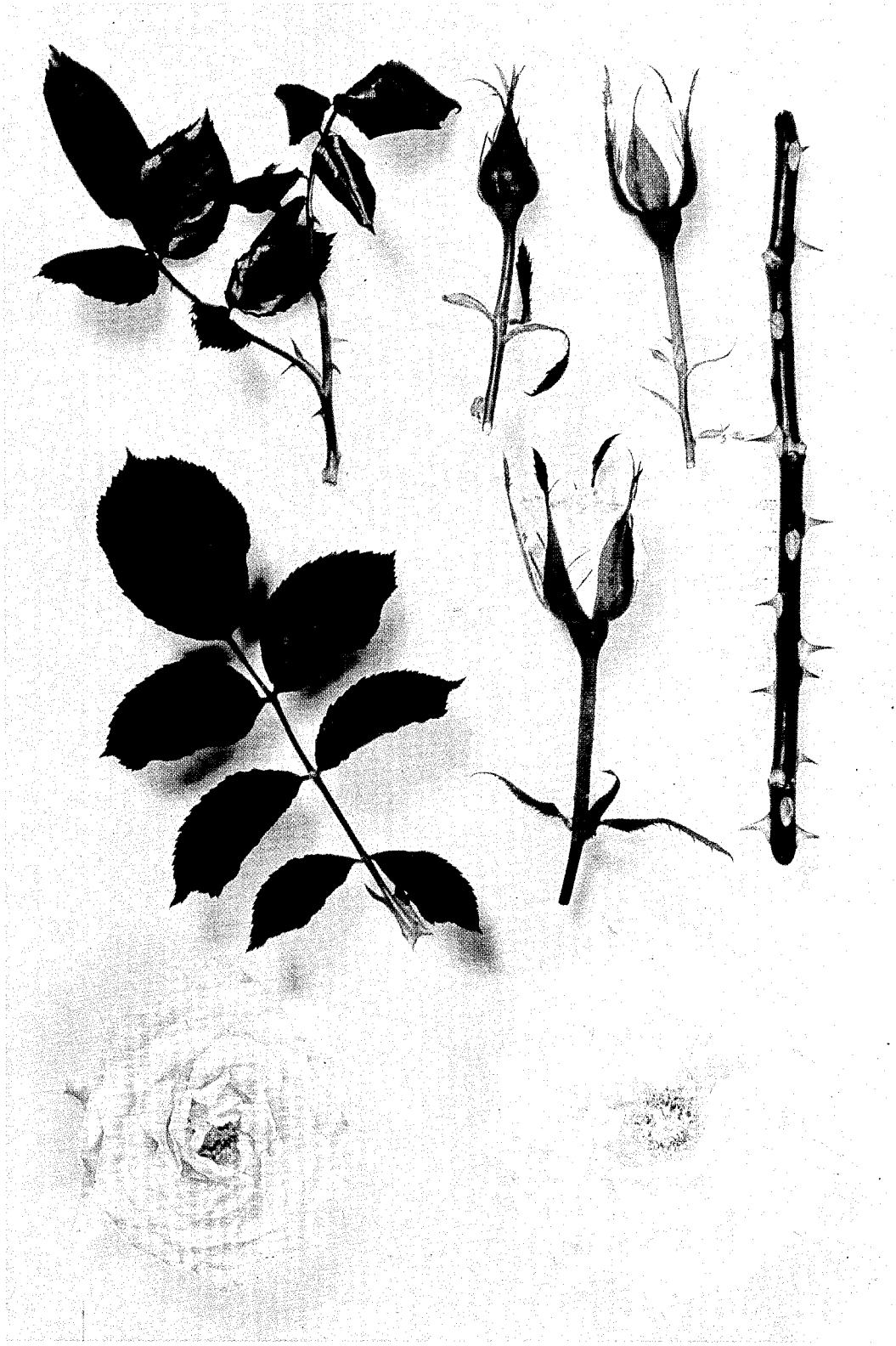

* * * * *